(12) United States Patent
Sengupta

(10) Patent No.: US 11,226,383 B2
(45) Date of Patent: Jan. 18, 2022

(54) ACTIVELY SHIMMED NEEDLES AND STYLETS FOR INTERVENTIONAL MRI

(71) Applicant: Vanderbilt University, Nashville, TN (US)

(72) Inventor: Saikat Tarun Sengupta, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 66 days.

(21) Appl. No.: 16/868,408

(22) Filed: May 6, 2020

(65) Prior Publication Data

US 2020/0355760 A1 Nov. 12, 2020

Related U.S. Application Data

(60) Provisional application No. 62/844,252, filed on May 7, 2019.

(51) Int. Cl.
*G01R 33/28* (2006.01)
*A61B 5/055* (2006.01)
*G01R 33/3815* (2006.01)
*G01R 33/3875* (2006.01)

(52) U.S. Cl.
CPC ............ *G01R 33/285* (2013.01); *A61B 5/055* (2013.01); *G01R 33/3815* (2013.01); *G01R 33/3875* (2013.01)

(58) Field of Classification Search
CPC .............. G01R 33/285; G01R 33/3815; G01R 33/3875; G01R 33/56536; A61B 5/055
See application file for complete search history.

(56) References Cited

U.S. PATENT DOCUMENTS

2008/0231277 A1* 9/2008 Yamamoto ....... G01R 33/56536
324/318

* cited by examiner

*Primary Examiner* — Susan S Lee
(74) *Attorney, Agent, or Firm* — Blank Rome LLP

(57) ABSTRACT

Artifacts caused by metallic needles used in MRI-guided procedures such as tumor biopsies significantly decrease the visibility of therapy targets and diminish the ability of the physician to accurately monitor and perform the procedure. As described in the present application, a needle including active shimming can self-compensate for these artifacts and significantly improve the visualization and monitoring of targeted tissue. The accuracy and overall outcomes of MRI-guided treatments can be significantly improved with the use of the needle.

20 Claims, 11 Drawing Sheets

(b)
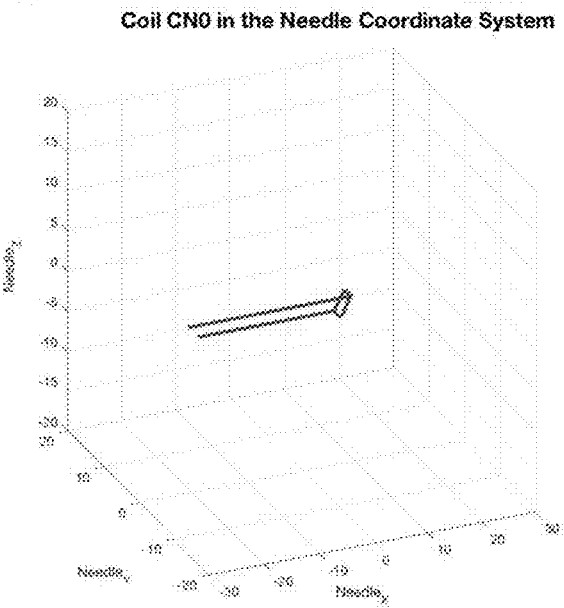
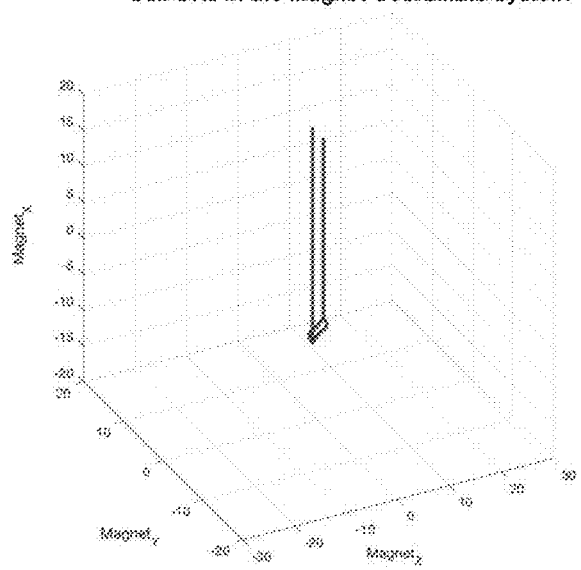
(c)
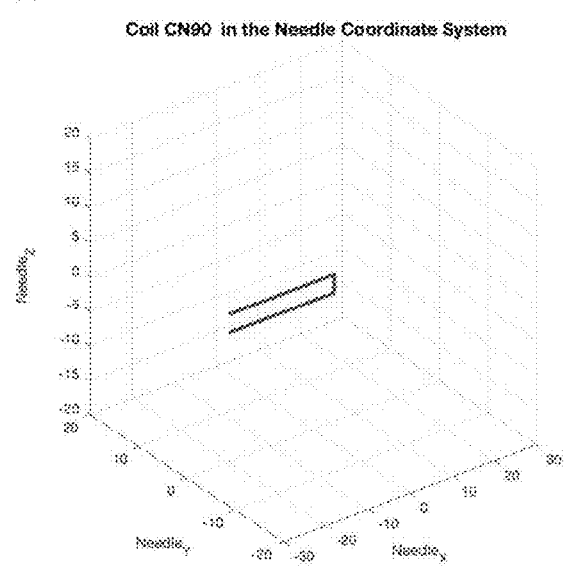
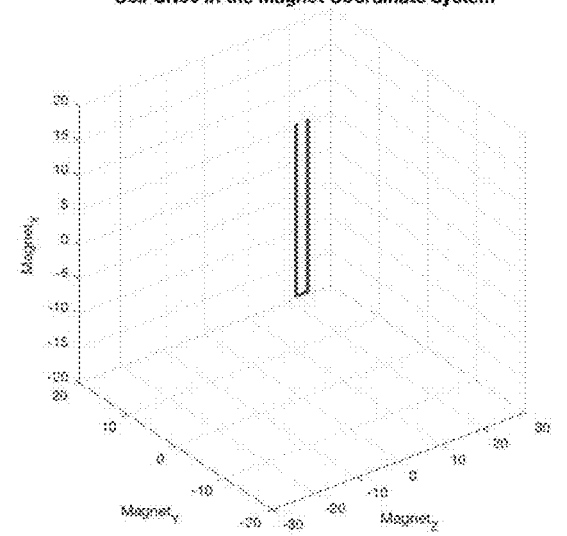
FIGS. 3B-3C

| Tip type | Needle | Stylet | Gauge | Material |
|---|---|---|---|---|
| 1 Flat | | | 9 - 14 G (3.7 - 2.1 mm O.D/ 2.9 - 1.6 mm ID) | Stainless Steel, Titanium, Nitinol, Brass |
| 2 One edge bevelled | | | | |
| 3 Conical | | | | |

FIG. 11

ACTIVELY SHIMMED NEEDLES AND STYLETS FOR INTERVENTIONAL MRI

CROSS REFERENCE TO RELATED APPLICATION(S)

This application claims priority to U.S. provisional patent application No. 62/844,252, filed on May 7, 2019, which is hereby incorporated herein by reference in its entirety.

GOVERNMENT SPONSORSHIP

This invention was made with government support under Grant No. NIBIB 1R21EB025258-01A1 awarded by NIH. The government has certain rights in the invention.

FIELD OF THE INVENTION

Embodiments are in the field of systems and methods for imaging. More particularly, embodiments disclosed herein relate to systems and methods for interventional MRI (iMRI) for improving visualization and monitoring of targeted tissue.

BACKGROUND OF THE INVENTION

Needle artifacts are a problem that impacts almost all interventional magnetic resonance imaging (iMRI) procedures. The underlying reason for the artifacts is the large magnetic field (B) deviation produced by the difference in magnetic susceptibilities between the MRI-compatible metallic needle and surrounding water-containing tissue. The artifacts caused by metallic needles used in MRI-guided procedures such as tumor biopsies and ablations significantly decrease the visibility of therapy targets and diminish the ability of the physician to accurately monitor and perform the procedure.

In particular, needle artifacts have been a long unsolved challenge in the field of iMRI. More specifically, the large difference in magnetic susceptibilities between an MRI-compatible metallic needle and the surrounding water-containing tissue induces significant magnetic field perturbations in the vicinity of the needle, which results in signal loss due to intra-voxel dephasing, image distortions and signal pile-ups due to voxel mis-mapping. These artifacts limit, to various extents, almost every iMRI procedure by obscuring and distorting targets and preventing accurate imaging of the region of interest. That results in reduced targeting accuracies, increased procedure times, inability to monitor therapy, and ultimately, a reduction in the efficacy of MRI-guided procedures.

Thus, it is desirable to provide a system and method for interventional MRI (iMRI) for improving visualization and monitoring of targeted tissue that do not suffer from the above drawbacks.

Advantages of the present invention will become more fully apparent from the detailed description of the invention hereinbelow.

SUMMARY OF THE INVENTION

Embodiments are directed to an actively shimmed needle system for iMRI. The actively shimmed needle system comprises a needle comprising a shaft having a longitudinal axis. The actively shimmed needle system also comprises at least one shim coil that extends along the shaft in a direction substantially parallel to the longitudinal axis. The at least one shim coil is configured to have voltage applied thereto to compensate for magnetic field distortion generated by the needle when the actively shimmed needle system is positioned within an operating MRI device.

Embodiments are also directed to a method of using an actively shimmed needle system for iMRI. The method comprises positioning an actively shimmed needle system within an operating MRI device. The actively shimmed needle system comprises a needle comprising a shaft having a longitudinal axis. The actively shimmed needle system also comprises at least one shim coil that extends along the shaft in a direction substantially parallel to the longitudinal axis. The method also comprises applying voltage to the at least one shim coil to compensate for magnetic field distortion generated by the needle when the actively shimmed needle system is positioned within an operating MRI device.

Additional embodiments and additional features of embodiments for the actively shimmed needle system for iMRI and method of using an actively shimmed needle system for iMRI are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It's understood, however, that the inventive concepts disclosed herein are not limited to the precise arrangements and instrumentalities shown in the figures. The detailed description will refer to the following drawings in which like numerals, where present, refer to like items.

FIGS. 3A-3D are CAD diagrams illustrating various views of a needle and 2-shim coil assembly;

FIG. 11 is a diagram illustrating exemplary needle and stylet geometries and materials.

DETAILED DESCRIPTION OF THE INVENTION

Figures 1A, 1B:
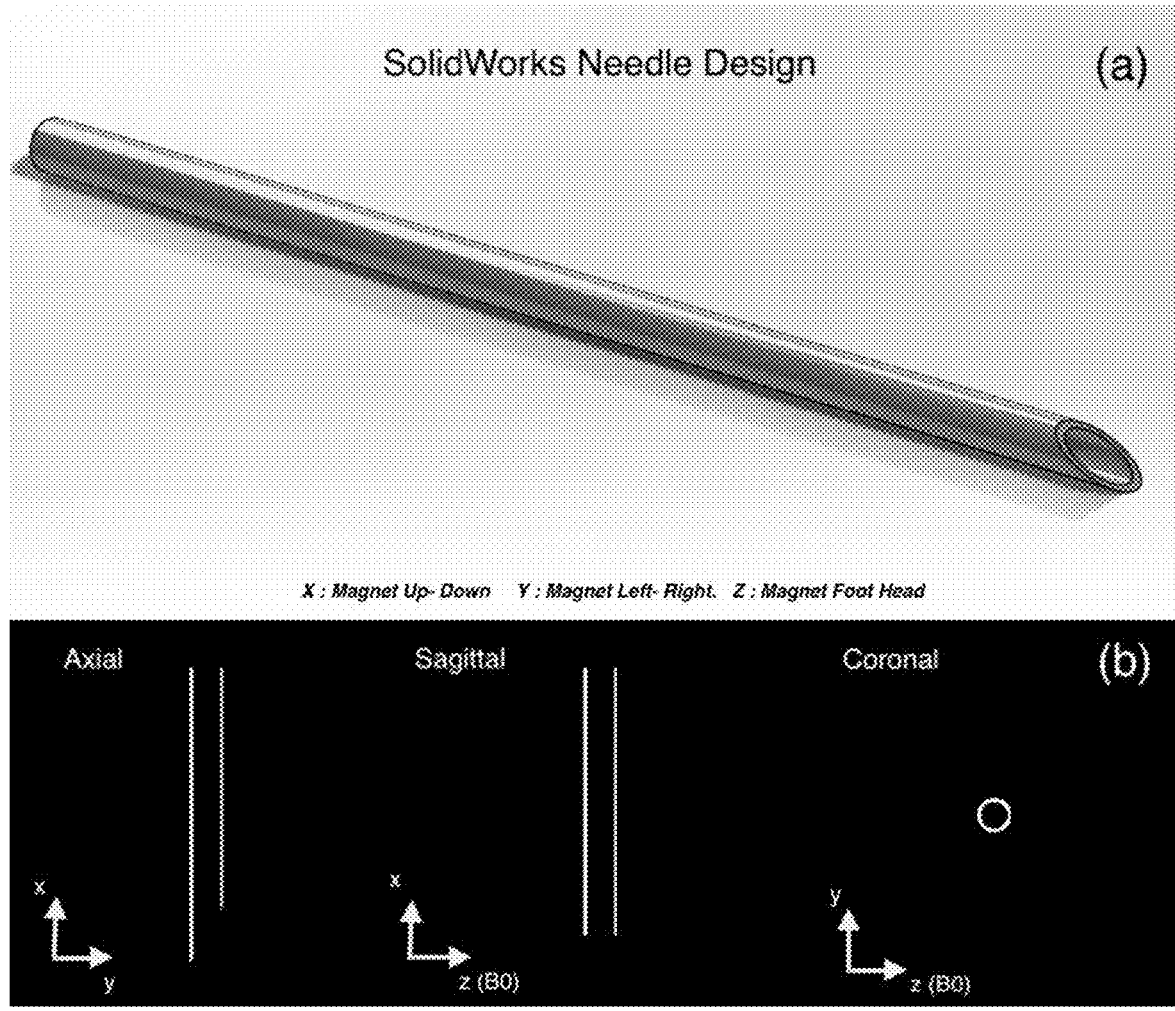
FIG. 1A is a computer-aided design (CAD) diagram illustrating a structure of a 10 gauge (10 G) needle (without coil)
FIG. 1B is a diagram of a voxelized needle grid of the needle shown in FIG. 1A in a scanner's coordinate system.

It is to be understood that the figures and descriptions of the present invention may have been simplified to illustrate elements that are relevant for a clear understanding of the present invention, while eliminating, for purposes of clarity, other elements found in a typical system for iMRI and a typical method of using a system for iMRI. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

There are potentially many different target areas/applications for the method/system described in this disclosure, although the breast serves as a majority of the focus herein for purposes of explanation.

For purposes of this disclosure, the terms "needle", "stylet", and "probe" (and respective derivatives thereof) may all be used interchangeably.

In this disclosure, a novel needle (system) design including active shimming is described which can self-compensate for the above-mentioned artifacts and significantly improve the visualization and monitoring of targeted tissue. The accuracy and overall outcomes of MRI-guided treatments can be significantly improved with the use of the needle.

In a simulation example, an active degaussing or shim insert is employed for simulating the compensation of needle-induced $\Delta B_0$ artifacts in a surrounding medium of water at an MRI field of 3 Tesla. Aim 1a of this example is dedicated to the simulation of needle and stylet induced magnetic field deviations at 3 Tesla that will include the influence of needle material, tip shape and orientation. Aim 1b will be focused on the simulation of shim fields and modeling of active shim coils that will compensate the field variations estimated in Aim 1a. A goal in Aim 2 will be the actual fabrication and testing of the needle and needle shim inserts, along with the appropriate electronics for operation of the DC shim coils during imaging. In-scanner calibration and phantom tests will follow bench testing for shim insert coils. Mitigation of artifacts induced by stainless steel, titanium, Nitinol and brass (or other paramagnetic or weakly magnetic material—even non-metal material that can produce a magnetic field distortion) needles and stylets will be demonstrated in gel phantoms at arbitrary orientations. Finally, a goal in Aim 3 will be the demonstration of needle artifact compensation in two different ex-vivo MR-guided studies, a biopsy targeting study and an MR thermometry precision experiment. The goal in the first will be to show improved qualitative and quantitative imaging of tissue around the needle and in the second will be to show improved precision of temperature measurements by image phase difference-based methods. This description solves the above problems via needle and stylet designs that are self-compensated for induced magnetic fields for use in a wide spectrum of iMRI applications at high magnetic fields.

Some novel features introduced in this description are:

1. The conceptualization of actively shimmed needles.
2. The design and optimization of the number and geometry of shim coils required to optimally shim a needle induced $\Delta B_0$ at, for example, 3 Tesla, taking into account the needle dimensions, tip shapes and material susceptibility. This will include target field methods to identify optimal coil patterns required to compensate the induced fields.
3. The estimation of current and voltage requirements, performance and limits of the individual shim coils.
4. The development of fabrication procedures of needles and stylets with shim coil inserts that are electrically insulated from the metal and the surrounding tissue.
5. The development of instrumentation required for supply of the shim coils and blockage of RF and gradient induced currents.
6. The design of new workflow for the use of such a needle, including pre-calibration, field characterization and current updates for arbitrary orientations.
7. The estimation of current and voltage requirements, performance and limits of the individual shim coils.

The negative impact of needle artifacts is felt in almost every iMRI procedure where a needle or solid stylet is employed. Therefore, this needle design can have applications in a variety of MRI-guided procedures including:

1. MRI-guided biopsies, where needle artifacts obscure tumor targets.
2. MR-guided Brachytherapy where pellet placement is compromised due to metal artifacts.
3. MR-guided radiofrequency, microwave and cryoablation where metallic probe artifacts obscure targets as well as compromise quantitative image-based monitoring of treated tissue.
4. Simultaneous Electrophysiology and Functional MRI in animal models where a needle is implanted for recording electrophysiological signals. Implanted needles cause significant artifacts in functional MRI images.
5. Any other MR-guided application where a metallic probe may be inserted into the body.

Introduction and Synopsis

Needle artifacts have long presented a persistent challenge in iMRI, and are caused by large magnetic susceptibility differences between metallic needles and stylets and the surrounding tissue. These artifacts obscure targets for example in biopsies and prevent accurate image-based monitoring in therapeutic applications. This disclosure presents, inter alia, the concept, design and modeling results of an active shim system for needles. Field disturbance induced by a titanium needle at 3 Tesla is modeled and an active orthogonal shim coil insert design is presented to demonstrate shimming of the field variation around the needle. The problem is therefore amenable to solving by a focused magnetic field shimming approach. A purpose of this disclosure is to therefore introduce a solution for this problem by developing active shim coils for iMRI needles and probes to correct the field disturbance caused by the needle.

Methods

A shim insert with DC coils will be described that will produce the necessary corrective field outside the needle.

Needle Design and Field Modeling:

FIG. 1A is a computer-aided design (CAD) diagram illustrating a structure of a 10 G needle (without coil). FIG. 1B is a diagram of a voxelized needle grid of the needle shown in FIG. 1A in a scanner's coordinate system. Midline sections in three orientations are shown. The needle is oriented in the base $\Theta_X=0°$, $\Theta_Y=0°$ and $\Theta_Z=0°$ orientation, where the angles represent needle rotations about the magnet's X (up-Down), Y (left-Right) and Z (foot-head) axes. White voxels representing the needle were assigned the magnetic susceptibility of titanium and black voxels were water.

More particularly, the shimming of a 10 G (3.4/2.7 mm outer diameter (OD)/inner diameter (ID)) titanium needle (Volume Susceptibility: $\chi=182*10^{-6}$) was modeled in a surrounding medium of Water ($\chi=-9.05*10^{-6}$). A 100 mm hollow needle was designed in SolidWorks® (Dassault Systemes®, MA, USA) with a 30° single sided bevel at the tip. The design was exported as an .STL file into MATLAB® (Mathworks®, MA, USA) and voxelized to yield a 3D grid of points defining the needle in space (FIG. 1). The voxel resolution was set to 0.1 mm. A sub-grid of 40 mm³ ($400^3$ voxels) was used for modeling the field from the top 3 cm of the needle. The field was modeled for two orientations with the needle orientated perpendicular to the $B_0$ field, along the magnet's up-down (X) axis. The field distortion was computed using Fourier-analysis-based field modeling at 3 Tesla.

Figure 3A:
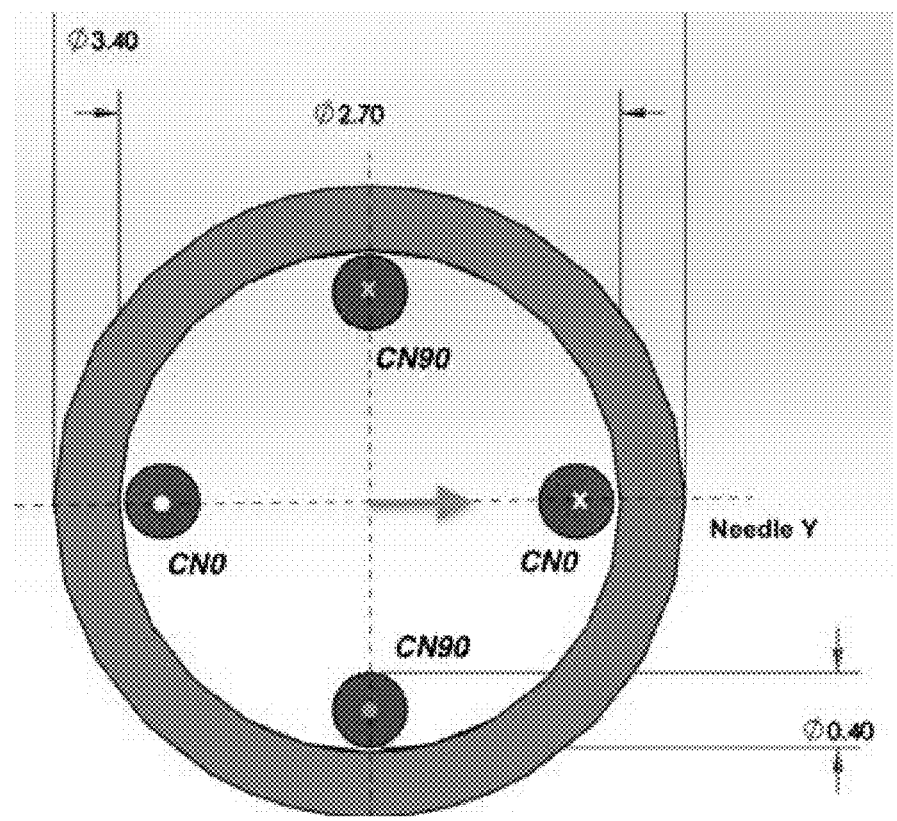
Figure 3D:
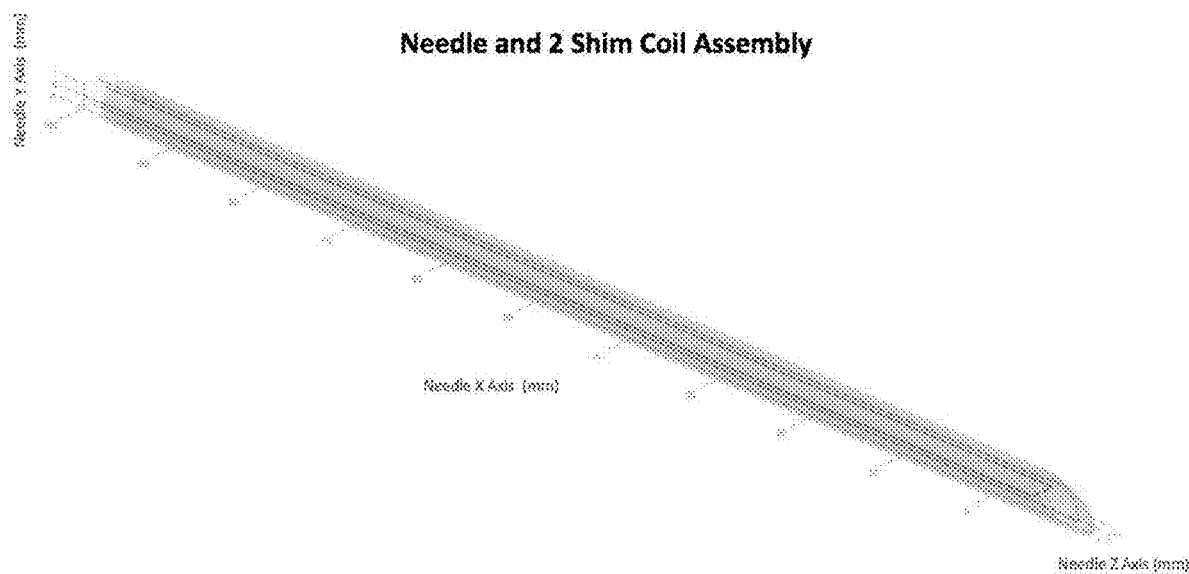

Shim Coil Design and Modeling:

FIGS. 3A-3D are CAD diagrams illustrating various views of a design of a needle and 2-shim coil assembly. FIG. 3A illustrates a sketch using Solidworks® of two shim coils in the needle's coordinate frame. All dimensions are in mm. $C_{N0}$ and $C_{N90}$ were designed orthogonally with the angle representing deviation from the needle's Y axis (centered arrow pointing to the rightward direction). Only one angle is used to define the coils since all coils will be designed orthogonal to the needle's radial plane. The X and O represent direction of current flow into and out of the plane; FIG. 3B illustrates $C_{N0}$ with split loop at the tip; FIG. 3C illustrates $C_{N90}$ in the needle and magnet coordinate frames; and FIG. 3D illustrates a semi-transparent perspective view of a needle and a 2-shim coil assembly.

More particularly, two shim coils with 26 G (0.4 mm OD) wire were designed in the needle's coordinate system ($X_N$: Along needle length, $Y_N$, $Z_N$: along radial directions) with normals along $Z_N(C_{N0})$ and $Y_N(C_{N90})$. $C_{N0}$ was designed with an angled split loop at its tip (with half the current in each arc) that followed the needle tip bevel. Coil geometry was transformed into the scanner's coordinate frame assuming a (0,0,0) degree orientation along the magnet's X axis. (again, see FIGS. 3A-3D). The field from each coil in the $400^3$ target grid was then estimated by using an implementation of Biot-Savart's field induction formula, with a current path resolution element of 0.4 mm. A current of 1 Amp was used to calculate the unit $B_z(r)$ field for both shim coils.

Field Shimming:

The field produced by the two shim coils were used to shim the needle induced field by multilinear least squares fitting in MATLAB® with a mask defined to exclude voxels within the needle. The currents were constrained to 600 mAmperes in each coil.

Results

Figures 2A, 2B:
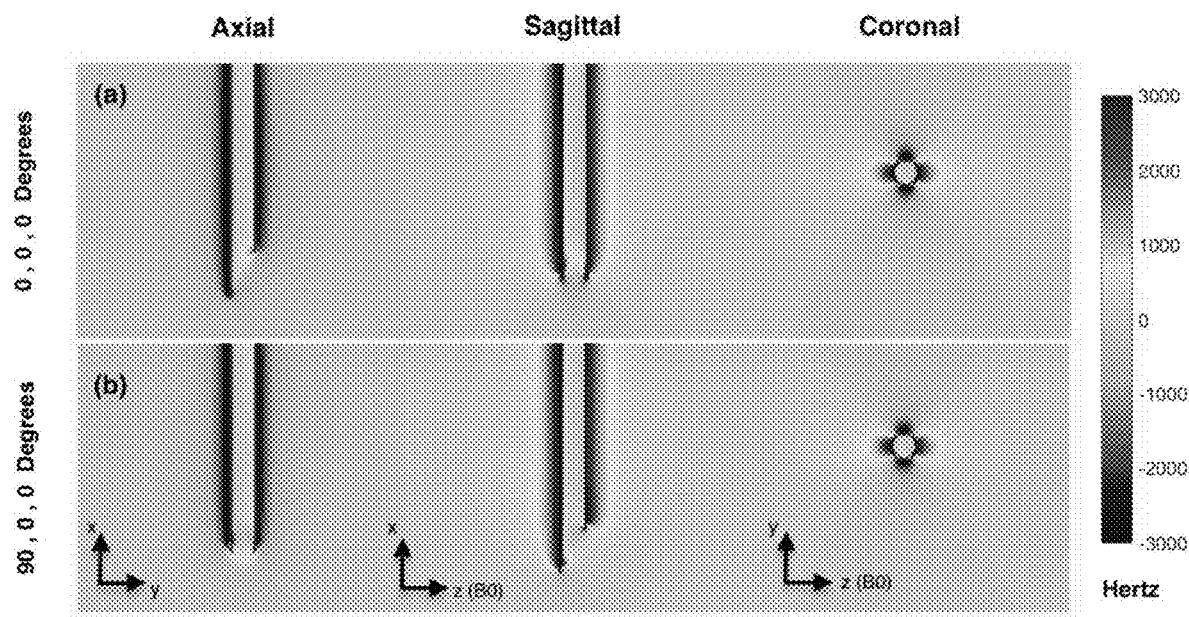
FIGS. 2A-2B are diagrams of the induced field produced by the needle (without coil) for two orientations.
Figures 4A, 4B:
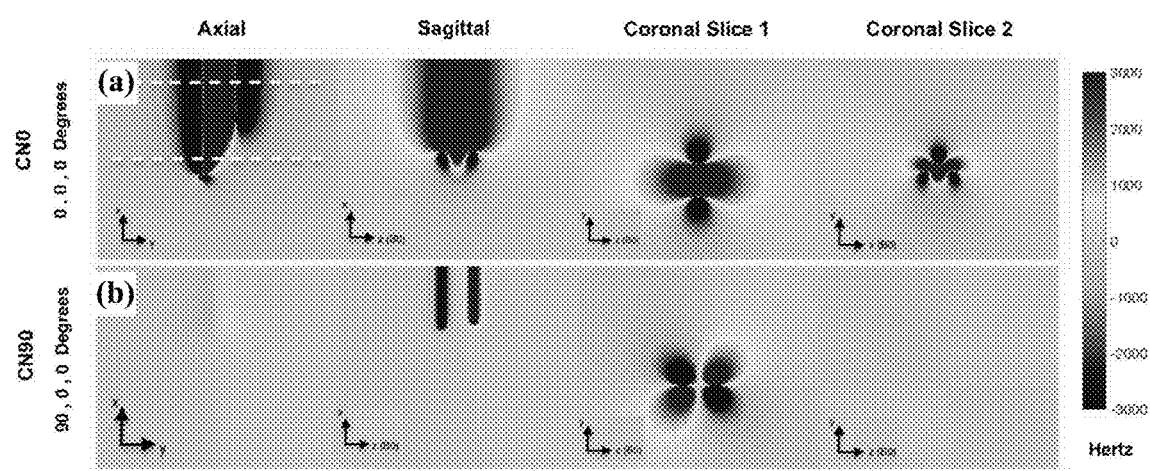
FIGS. 4A-4B are diagrams of the induced field produced by the needle and 2-shim coil assembly, for two orientations.

FIG. 2 shows the modeled $\Delta B_0$ of the needle for two orientations. More particularly, FIG. 2 illustrates estimated needle (without coil) induced field at 3 Tesla for the two orientations. Midline sections in three orientations (via axial, sagittal, and coronal slices) are shown. Note that the dipolar pattern observed in the midline coronal slice does not change with orientation due to needle symmetry at this X position. The resolution is 0.1 mm/voxel isotropic. The familiar dipolar pattern is observed that varies with needle orientation. FIGS. 4A-4B are diagrams of the induced fields produced by the needle and 2-shim coil assembly described above and in FIG. 3 for 1 Amp, for two orientations. More particularly, strong field variation is seen in both cases. Coronal slices are shown at two levels indicated in the top left axial frame by white dotted lines. Note in Coronal slice 1 that $C_{N0}$ produces a field in phase with the needle's induced field (FIG. 2 Coronal slice). However, as the needle and the shim coils rotate about the X axis, the $C_{N0}$ field no longer matches the needles field. $C_{N90}$ is now required to produce the corrective field. The field variation is similar to that induced by the needle, which indicates the feasibility of shimming. Note that while the $C_{N0}$ field matches the needle $\Delta B_0$, the $C_{N90}$ field has a phase offset. As the needle is rotated about the X axis, the two coils therefore perform in a phased manner.

Figures 5A, 5B, 5C, 5D:
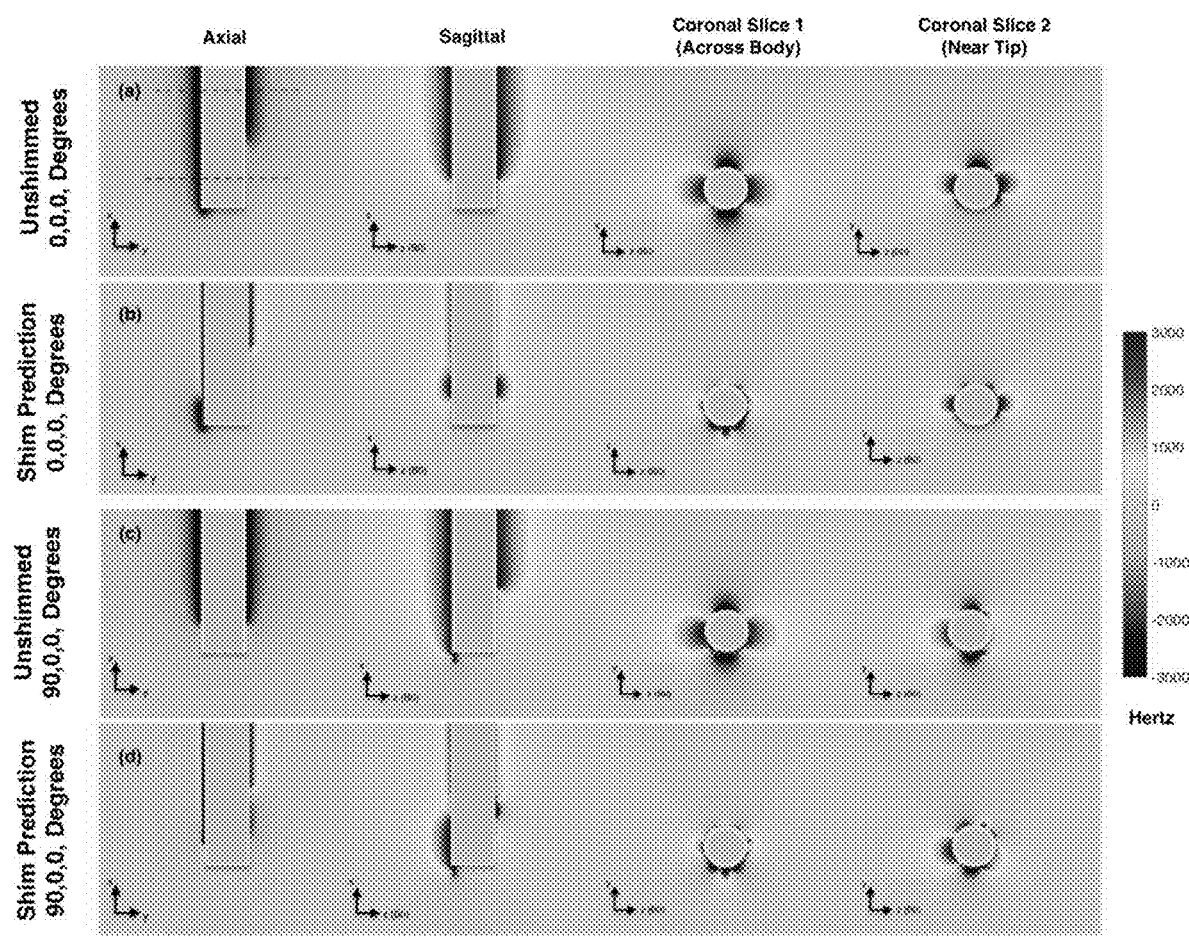
FIGS. 5A-5D are diagrams of a comparison of induced fields produced by the needle (without coil) and with a 2-shim coil assembly, for two orientations.

FIGS. 5A-5D show the results of shimming. The figures are diagrams of a comparison of induced fields produced by the needle (without coil) and with a 2-shim coil assembly, for two orientations. More particularly, FIGS. 5A-5D show results of simulated needle shimming (using 2-shim coil configuration of FIG. 3) for orientation 1 (FIG. 5A and FIG. 5B) and orientation 2 (FIG. 5C and FIG. 5D). The grey voxels (centered within the needle's OD) represent the mask used to exclude the voxels within the needle's OD. Good compensation of the field inhomogeneity is predicted around the needle for both orientations, at all sections of the needle. For orientations at which $\Theta_Y$ and $\Theta_Z \neq 0°$, a third coil may be required to shim the tip well while concurrently not damaging the shim more proximally at the body of the needle. Also, the required currents are expected to be halved for 1.5 Tesla MRI. For example, the currents may be in the range of +/−250 mAmps.

There is good correction of the $\Delta B_0$ induced by the needle in both orientations. The standard deviation of the field outside the needle was reduced from 334.6 Hz to 178.7 Hz for orientation 1 with currents of 510 mA and 2 mA and from 335 Hz to 192 Hz for orientation 2 with currents of 0 mA and 494 mA for $C_{N0}$ and $C_{N90}$, respectively. A small uncompensated field remained at the tip of the needle where the coils did not reach.

Discussion

The results presented here demonstrate the feasibility of shimming a needle with active shim coils. Generalized coil paths can be designed to provide robust shimming for all needle orientations, including ones designed using target field and stream function methods. The wire sizes and current constraints will clearly scale with needle size. For the 26 G wire used here, the current capacity is ~505 mA assuming a coefficient of 500 circular-mils/Amp.

Further Description

This disclosure has a highly innovative concept of applying degaussing technology to shim interventional needles.

This disclosure employs 3D F SE-based MSI as the primary technique to image as well as map the fields around the needle, although it is noted that any imaging sequence should demonstrate artifact mitigation. The initial data below on a 3 Tesla scanner demonstrates imaging and field mapping near a stainless steel needle in a gel phantom. It is believed that using MSI significantly improves the rigor of this work.

Evaluation of Shimming:

3D MSI is the primary technique to image and perform field mapping around the needle and allows for much more rigorous evaluation of shimming efficiency. The inventor has included a list of methods to use to evaluate shimming efficiency. These include statistical comparisons on the: 1) residual signal voids in sum-of-squares images and comparison of signal histograms for evaluating changes in signal voids and pileups; 2) statistical comparison of field maps computed by the center of mass method; and 3) statistical comparison of in-plane and slice distortions using a grid phantom and polyethylene needles as gold standards for comparing distortions.

Feasibility:

Simulations have been provided of field distortions induced by a 14 G titanium needle placed perpendicular to $B_0$, i.e., the field produced by a single turn of wire running along the length of the needle and the final shimmed field around the needle. The field distortion is shown to be almost perfectly shimmed with only −199 mA of current in the coil. Shimming of stainless steel that has much higher susceptibility is also addressed.

Specific Aims

As mentioned above, a goal of this disclosure is to develop a method to correct susceptibility artifacts and signal loss produced by metallic needles in MR-guided interventions by designing an active shim insert for compensation of needle-induced $\Delta B_0$.

Needle and stylet artifacts have been long unsolved challenges in iMRI. The metallic needle in the scanner's field creates a field distortion and a variety of susceptibility artifacts in tissue including signal loss, distortions and signal pileup around the needle. These artifacts cause problems in many interventional procedures by obscuring target tissues. In MR-guided biopsies, they lead to missed targets, larger than necessary tissue resections and longer procedure times. In MR-guided ablation, they prevent accurate real time monitoring of temperature by MR thermometry. In MR-guided brachytherapy, they cause misplacement of radioactive seeds. Importantly, these artifacts essentially impact every procedure where a needle or stylet is introduced under MR guidance. Needle artifacts are the main reason why most interventional procedures are still performed at 1.5 Tesla, even though much higher SNR and imaging resolutions are available at 3 Tesla.

Needle artifacts fall under the larger category of metal artifacts in MRI and existing metal artifact reduction techniques such as MARS, MAVRIC/MAVRIC-SL, SEMAC, VAT could in principle be applied to partially tackle this issue. However, these sequences are primarily based on time-consuming 2D/3D FSE and therefore are not suitable for MR guidance applications where high speed of imaging is important for dynamic 3D tracking (e.g. for biopsies and bolus tracking) or continuous quantitative imaging (e.g. thermometry). There have been some efforts to design needles with a diamagnetic bismuth coating to compensate the induced field distortions. However, such needles suffer from bio-compatibility and mechanical strength issues.

Essentially, there exist few general solutions to this problem from the needle or stylet design point of view.

A goal is to therefore show that the use of active shimming coils inserted in a needle or stylet can compensate the induced field distortions and reduce signal losses and image distortions around the needle. A framework, fabrication procedure and instrumentation for actively shimmed metallic needles and stylets may be used for a range of MR-guided interventions. The experiment involves the following specific aims:

Aim 1: Simulate Needle- and Stylet-Induced Field Distortions and Shim Coils for Field Correction.

i) The magnetic field distortion created by MR-compatible thin-walled needles and solid stylets with a hollow core at 3 Tesla is modeled for arbitrary orientations. Four materials, namely titanium, Nitinol, stainless steel and brass, and different tip designs and gauges, will be modeled.

ii) Degaussing of coil fields, coil positions and current requirements for 3D compensation of the needle and stylet-induced $\Delta B_0$ is simulated and optimized.

Aim 2: Fabricate, Calibrate and Test Self-Shimmed Needles and Stylets in Phantoms.

i) This disclosure describes the fabrication of: a) MR-compatible thin walled needles; and b) MR-compatible stylets with hollow cores from stainless steel, titanium, Nitinol and brass.

ii) Shim inserts are fabricated for the above with insulated conducting tracks based on the modeled designs.

iii) A DC shim current supply system is assembled with integrated stability and safety mechanisms.

iv) The shim coils are calibrated in the scanner with 3D FSE-based MSI and field mapping.

v) MSI tests are performed to demonstrate reduced $\Delta B_0$, and signal void and distortion artifacts in phantoms.

Aim 3: Demonstrate Compensation of Needle Artifacts in Ex-Vivo Studies of Porcine Muscle.

The following experiments demonstrate compensation of artifacts at 3 Tesla.

i) An ex-vivo biopsy experiment of randomly selected target points in porcine muscle tissue with 3D FSE-based MSI to show reduction in $\Delta B_0$ and signal void/pileup with shims ON versus shims OFF.

ii) Measurement of temperature precision in GRE MRI phase-based thermometry in porcine muscle tissue to show higher precision of temperature measurements with shims ON versus shims OFF.

Research Strategy—Significance

Needle Artifacts are a Recognized Unsolved Challenge in the Field of iMRI.

The large difference in magnetic susceptibilities between a paramagnetic metallic needle or stylet and the surrounding diamagnetic tissue induces significant field perturbations in the vicinity of the needle. This field perturbation causes a range of susceptibility artifacts, including signal loss, in-plane and slice distortions and signal pileups due to voxel mis-mapping. The severity of the artifacts scales linearly with field strength, since $\Delta B_0$ is directly proportional to field strength, which is a major reason why most iMRI procedures remain restricted to <3 Tesla, even though much higher SNR and voxel resolutions are achieved at 3 Tesla and above.

The Negative Impact of these Artifacts is Felt in Almost Every iMRI Procedure where a Hollow Needle or Solid Stylet is Employed.

Figure 6:
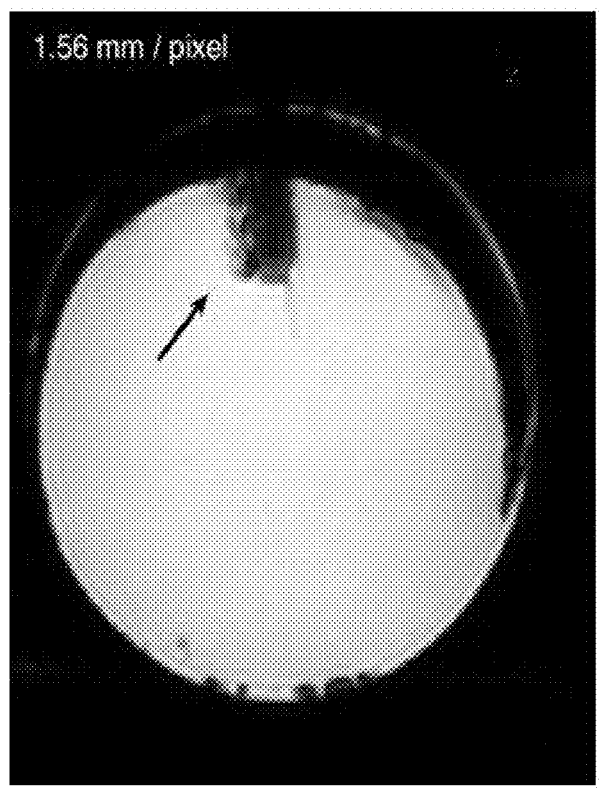
FIG. 6 is an image of an MRI illustrating a needle artifact.

In MR-guided biopsies, artifacts obscure target lesions, vital anatomies such as nerves and vessels and the actual device position. In core needle breast biopsy at 1.5 Tesla for example, it has been reported that the void (needle artifact)

caused by a 14 G (2.11 mm OD) needle was 4 mm, which caused small targets to disappear and large targets to be distorted. At 3 Tesla, the signal void around a 14 G breast biopsy needle has been reported to be as large as 9.5 mm. FIG. 6 shows an artifact of approximately 20 mm caused by a 2.5 mm OD Nitinol needle in the 3 T scanner. Clearly, biopsies of lesions <1 cm can be severely hampered by such a large artifact. These artifacts assume more importance in the light of a recent trend toward vacuum-assisted breast biopsies that employ even larger needles (8-12 G/4.19-2.77 mm OD) and suffer from significantly worse artifact levels. Similar issues with needle artifacts have been discussed in MR-guided prostate, head and neck, musculoskeletal, spine and liver biopsies. Susceptibility artifacts also create difficulties in MR-guided brachytherapy. Both the stylet and the radioactive pellet are usually metallic (e.g., titanium stylet and iridium source in a steel or titanium capsule) and generate signal voids making placement under MR-guidance difficult and inaccurate. Since the placement is actually guided by the pellet artifact position, it can result in large errors in seed placement and reduced treatment efficacy. It has been reported that the deviation of a 3 mm pellet position from the center of mass of the induced signal void at 1.5 Tesla to be up to 1.9 mm. A whole range of MR-guided therapeutic applications such as radiofrequency, microwave and cryo-ablation also suffer from susceptibility artifacts and the artifacts are especially damaging close to the probe where it is most important to monitor temperature and tissue damage in real-time. MRI phase-based thermometry is either made impossible by the signal void or inaccurate due to high phase noise. Another area of high interest where needle artifacts are extremely limiting is simultaneous electrophysiology/nerve stimulation and functional MRI (fMRI) in animal models. fMRI relies on $T_2^*$ contrast-based imaging, that is extremely vulnerable to $\Delta B_0$. It is of most interest to get functional information closest to the probed site, which is impossible with current needle designs. In summary, needle artifacts are a long-standing challenge in iMRI and they hinder a wide range of diagnostic, therapeutic and basic research applications. Any general technique to correct these artifacts without adding to procedure times will have a significant impact across the field of iMRI. As a solution to this challenge, the $\Delta B_0$ and the artifact produced by the needle can therefore be potentially corrected by current carrying degaussing or shim coils within the needle.

Compensation of Needle Artifacts: State of the Field:

Needle artifacts fall under the larger category of metal artifacts in MRI and therefore, existing metal artifact reduction techniques such as MARS, MAVRIC/MAVRIC-SL, SEMAC, VAT and parameter adjustments like changing readout direction, RF bandwidths and needle orientation with respect to $B_0$ could be, in principle, applied to partially tackle this issue. However, these sequences were developed for anatomical imaging of implants and are primarily based on time-consuming 2D Spin Echo (SE) and 2D/3D FSE and therefore not suitable for iMRI applications where high speed of imaging is important for either dynamic 3D tracking (e.g. in biopsies, bolus tracking) or continuous quantitative imaging (e.g. in thermometry). These sequences also do not provide $T_2^*$, phase contrast that is important in many applications. Therefore, a compensation method that tackles the issue at the source, i.e., the needle, would be significant in enabling a) imaging with a variety of sequences beyond SE/FSE; b) imaging at a high frame rate; and c) pushing these applications to higher field scanners. The above sequences are nevertheless the state of the art in imaging around metals and therefore can serve as perfect evaluation tools for any artifact-reduction method. In this work, 3D FSE-based MSI is used to evaluate the corrections. (Aim 2). With regard to compensation of needle artifacts in particular, while they have been characterized in several studies, there have been very few presented solutions that satisfy the speed and sequence requirements of iMRI. Titanium needles have been shown to produce less artifact than stainless steel and Nitinol, but the level of artifact is still significant. Glass and plastic needles have lesser artifacts, but are mechanically weak. One of the rare proposed solutions was to coat paramagnetic titanium with diamagnetic bismuth to produce a composite material needle. However, unanswered questions regarding mechanical strength and biocompatibility prevented further adoption of this design. This is therefore still a problem open to new solutions.

A goal is to demonstrate self-shimmed metallic needles and stylet with shim inserts and show qualitative and quantitative compensation of needle artifacts in phantom and ex-vivo MR-guided experiments.

Research Strategy—Innovation

An innovation in this disclosure is the application of degaussing to minimize needle artifacts in MRI-guided interventional procedures. Needle artifacts have been a long-standing issue in this field and there have been almost no solutions to this problem, especially from the needle design point of view, to enable fast volumetric imaging. This disclosure aims to solve this issue by integrating an active shim coil insert in a needle in order to correct the field deviation outside of it.

The needle design will introduce novel features that will benefit the accuracy and workflow of MR-guided interventional procedures in at least the following several ways.

1. Shimming of the $B_0$ field distortions around the needle, leading to reduction of artifact levels and improved visualization of the needle, the surrounding tissue, sensitive anatomical structures like blood vessels and nerves and most importantly, the intervention target. That will be especially helpful at 3 Tesla and higher fields where susceptibility artifacts are severe.

2. Adjustable current in the needle shim coil for adaptive field correction. If required, the shim coils may also be turned off to visualize the needle artifact.

3. Since the induced $\Delta B_0$ field as a function of needle orientation with $B_0$ is fixed and predictable, the shim coil currents can be pre-calibrated to adapt to needle orientation, enabling seamless artifact correction and allowing a larger range of approach angles.

4. Minimization of $\Delta B_0$ around the needle will allow for improved quantitative monitoring of tissue around it, for example in temperature monitoring in MR-guided ablation.

5. Minimization of $\Delta B_0$ around the needle will open up the possibility of employing a wider range of imaging sequences for improved tissue visualization and characterization, including low acquisition bandwidth sequences that are not used in image guidance due to their sensitivity to $\Delta B_0$. It may be possible to use such sequences to get supplemental information on biopsy and therapy targets.

The novel work described in this disclosure will generate previously unknown knowledge regarding: 1) the number and geometry of shim coils required to optimally shim a needle-induced $\Delta B_0$ at 3 Tesla, taking into account the needle dimensions, tip shapes and material susceptibility; 2) the current and voltage requirements and limits of the individual shim coils; 3) fabrication procedures of needles and stylets with shim coil inserts that are electrically insulated from the metal and the surrounding tissue; 4) the instrumentation required for supply of the shim coils and blockage of RF and gradient induced currents; and 5) workflow for the use of such a needle, including pre-calibration, field characterization and current updates for arbitrary orientations.

In summary, the proposed needle design will benefit a large spectrum of iMRI applications.

Research Strategy—Approach

Aim 1: Simulate Needle and Stylet-Induced Field Distortions and Shim Coils for Correction.

Simulation of induced field distortions: Simulations may be performed in MATLAB® to predict the 3D field distortions produced by hollow needles and solid stylets in the MR environment with a surrounding medium of water. Fourier-analysis-based field modeling may be used since it is computationally efficient, allows for heterogeneous, arbitrarily shaped samples and is most straight forward to implement. The method first estimates the induced magnetic field in the Fourier domain, B(k), followed by a 3D FFT to obtain the spatial domain induced field B(r). While a wide variety of needle/stylet materials and tip types may be employed, the simulations employ a set of three basic representative tip geometries and four materials, as shown in FIG. 11. However, these are exemplary needle and stylet geometries, and materials. It is noted that other geometries and materials may alternatively be employed. The examples shown in FIG. 11 closely resemble designs used in the clinic. For example, the commonly used 'Chiba' needle is a one sided 25° beveled needle, similar to design #2 in FIG. 11. Stylet designs will be simulated with an internal slot for shim insert placement. A full range of triaxial orientations with respect to $B_0$ will be modeled.

Simulation of field correction coils: Geometries of field correction coils to be placed on the needle insert will be based on degaussing coil designs described above. The field B(r) produced by the wire paths will be simulated using a discretized Biot-Savart's approach used in degaussing coils and recently developed local shim coils in MRI. Only Bz(r) is of interest since it is the component related to image and needle artifact generation in MRI. Initial solutions will include simulation of three orthogonal coil paths: 1) A single zN axis coil running circumferentially around the needle near the needle tip, similar to the L loop in FIG. 6; 2) An xN axis coil running along the needle length; and 3) A yN axis coil orthogonal to the xN and zN loops. Fields produced by these individual coils will be simulated and the total field produced at any point outside the needle will be the summed field from all three coils. While the initial solution will have one single-turn coil per axis, the optimal number of required coils, turns per coil and their placement will be determined by simulating various coil configurations. An important parameter will be the current carrying capacity of the conductor given the space constraints inside a needle. A 26 G/0.4 mm diameter copper wire for example has a current carrying capacity of ~500 mA, based on assuming a moderate 500 circular-mils/A. Simulations will be performed to determine the optimal wire gauges for each needle size. The shimming process will involve a multiple linear least squares regression that fits the needle induced $B^T_z$ (Target Bz(r)) predicted by simulations to the fields produced by the three coils. Therefore, $$B_z^T = CB_z \ \& \ C = [B_z'B_z]^{-1}B_z'^{*}B_z^T \quad (1)$$

where $B_z$ is the matrix of fields produced by the three shim coils when unit (1 A) current is flowing through them, and C is the vector of coefficients representing the current requirements. Since the induced field from a needle should be predictable for any orientation, the corresponding shim currents can also be estimated a-priori and used to populate a lookup table. Given the needle orientation during a procedure, this table can be used to adaptively compensate for orientation dependent changes in induced fields.

New Simulations Supporting the Feasibility of the Concept.

Figures 7A, 7B, 7C, 7D:
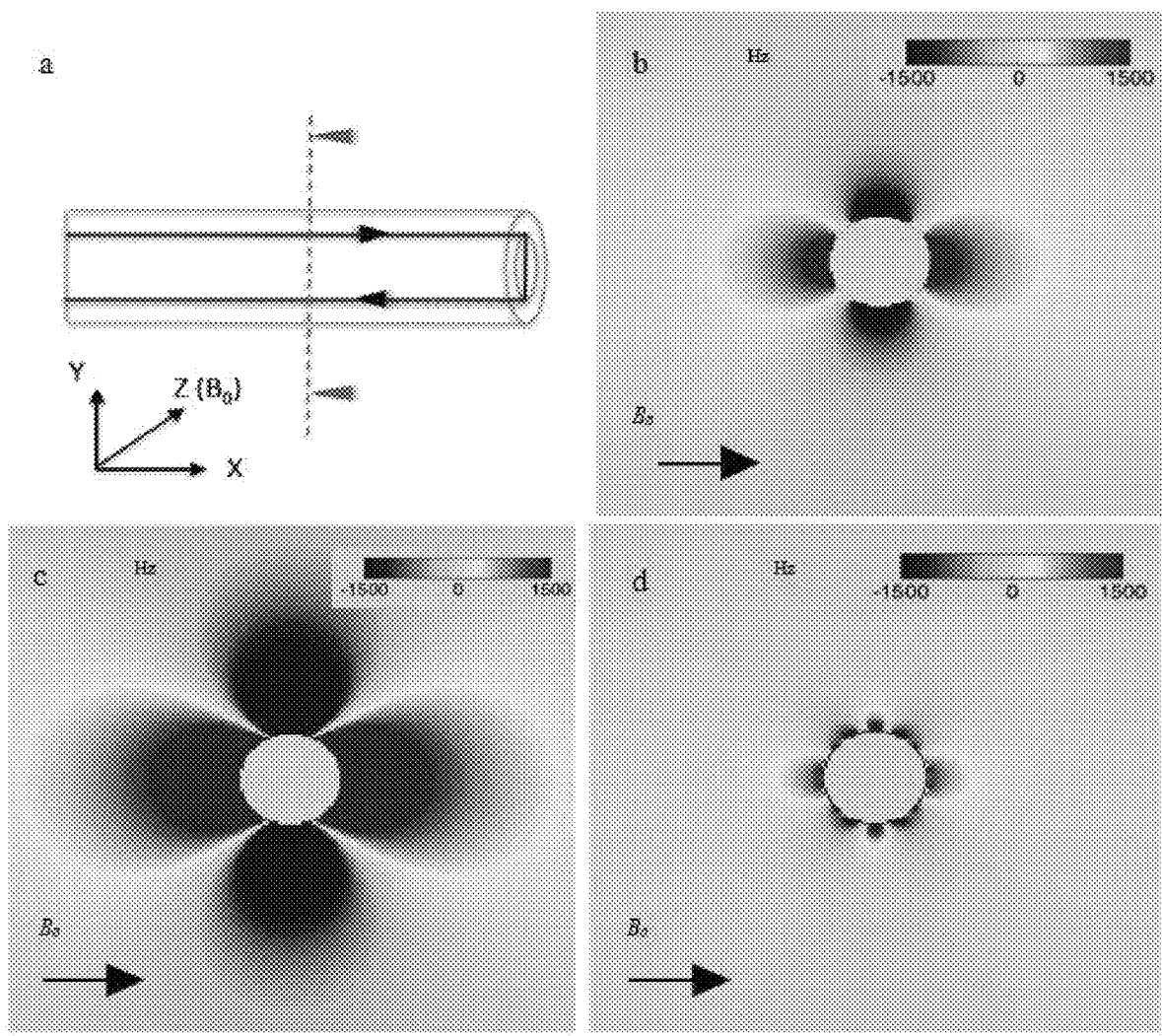
FIGS. 7A-7D are diagrams illustrating a titanium needle having a single loop shim coil (FIG. 7A), field variation induced by the needle (FIG. 7B), field produced by the shim coil (FIG. 7C), and final predicted shimmed field with −199 mA current in the coil (FIG. 7D)

With respect to FIGS. 7A-7D, a simulation of needle-induced $\Delta B_0$, fields produced by a current loop and field shimming are illustrated using the techniques mentioned above. FIG. 7A illustrates a 14 G titanium needle placed perpendicular to $B_0$. The black line indicates a single loop shim coil in the XY plane carrying current in the direction shown by black arrowheads. The FOV was 12 mm, voxel resolution was 0.05 mm. FIG. 7B illustrates a field variation induced by the needle in Hz at 3 Tesla visualized in the YZ plane. FIG. 7C illustrates a field produced by the shim coil carrying 1 Amp. FIG. 7D illustrates a final predicted shimmed field with −199 mA current in the coil.

More particularly, the field induced by a 14 G (OD/ID 2.11/1.60 mm) titanium ($\chi$=182 ppm) needle placed perpendicular to $B_0$ is estimated. Next, the field produced by a single turn loop of wire in the XY plane carrying 1 A was simulated and finally, a fit according to Eqn. 1 was performed to predict a nicely shimmed field with a current of −199 mA. That is well under the current carrying capacity of 0.4 mm, 26 G enameled copper wire which is estimated to be 337 mA (using a very conservative 750 circular-mils/A) and 505 mA (using a moderate 500 circular-mils/A). A 26 G wire loop can easily fit inside the 14 G needle with 0.8 mm clearance. The simulation demonstrates the feasibility of the idea at 3 Tesla for titanium, and materials with susceptibilities around that of titanium, such as Nitinol (245 ppm) and brass (−16 ppm).

Limitations and Alternative Strategies: The most challenging material to shim would be stainless steel which has a susceptibility of ~1500 ppm (316 non-magnetic steel). The simulations predicted the best-case shimming of a 14 G stainless steel needle at 3 Tesla to require −1.57 A which would exceed the space constraints. However, a significant ~40% reduction in the standard deviation of the induced field could be achieved by constraining the current to ±0.8 A (needing 24 G, 0.5 mm wire). Therefore, significant reduction of the induced inhomogeneity and susceptibility artifacts with stainless steel needles is expected as well, especially farther away from the needle with practical wire sizes using only one turn. The current limits should scale with field strength making the gains better at 1.5 Tesla. Also, compromises can be made on the extent to which the field needs to be shimmed and a point of diminishing return can be identified. Another strategy would be to pursue coil design methods such as stream function or target field methods and singular value decomposition (SVD) analyses to find minimum current solutions. A third strategy would be to concentrate only on the needle tip, since that is the most important location to obtain image information from.

Aim 2: Fabricate, Calibrate and Test Self-Shimmed Needles and Stylets in Phantoms.

2a. Needle and Stylet Fabrication and Induced Field Measurement: 9-14 G (OD/ID 3.76/2.99 mm, −2.11/1.60 mm) needles and stylets will be constructed out of stainless steel, Nitinol, titanium and brass, materials commonly used in iMRI procedures. All these tubes can be purchased from manufacturers off the shelf. The tubes will be machined to lengths of 10 cm and cut to beveled designs shown in FIG. 11. For the stylets, solid machined tips will be welded onto thick-walled tubes with central hollow cores for the shim inserts. Hand-held permanent magnets will be used to confirm that the needles are not non-ferromagnetic.

Figures 8A, 8B, 8C:
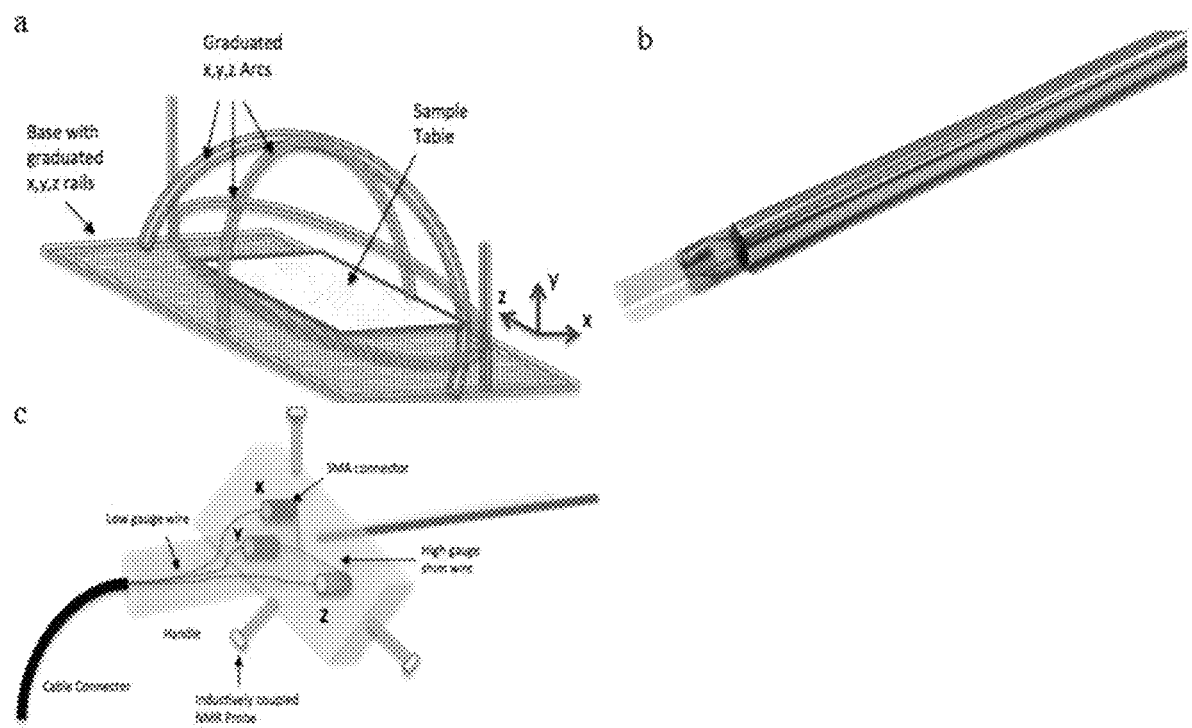
FIGS. 8A-8C are diagrams respectively illustrating a guide frame, actively-shimmed Nitinol (nickel-titanium alloy) needle, and a needle connector box.

All experiments will be performed on a 3 Tesla whole body scanner with a 2-channel body transmit/receive coil (Philips® Healthcare, OH, USA). The first set of tests in the scanner will be to validate the field simulations of Aim 1a. The inventor will 3D print a graduated triaxial guide frame (FIG. 8A) to enable needle insertions at various angles outside the bore. The base and arcs of the guide frame will be graduated for linear and angular positioning. FIG. 8B illustrates a 12 G Nitinol needle with a 15 G polyimide insert and a 36 G, 10-turn coil. FIG. 8C illustrates a needle connector box which is discussed more fully below. All experiments will have the following general steps: 1) landmark to center of the sample table containing the sample/phantom and move table to scan position; 2) perform 3D imaging and locate the target(s) coordinates offline and estimate insertion depths for desired angles; 3) move table out of the bore, translate guide frame arcs to target x, y, or z and insert needle at desired angle along the arc to estimated depth; 4) secure needle in place using arc screws; and 5) move table into bore and perform imaging.

Imaging of the Needle and Artifact.

Figure 9:
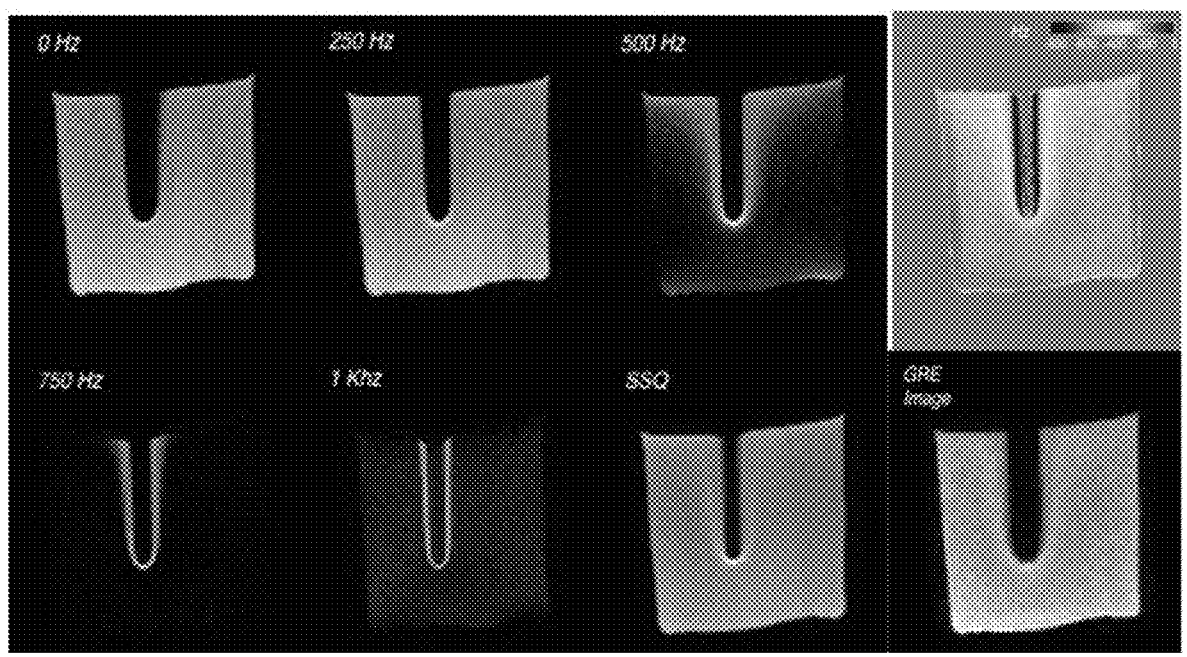
FIG. 9 illustrates 3D Fast Spin Echo (FSE)-based Multi-spectral Imaging (MSI) images of a stainless steel needle in a gel phantom using various fixed frequency offsets. A sum of squares (SSQ) image, gradient echo (GRE) image, and a generated field map are also shown.

A 3D FSE-based MSI is used to image the needle. A set of fixed frequency offsets will be used and an SSQ image will be evaluated. FIG. 9 shows an axial slice from a 3D MSI of a 2.19 mm/1.3 mm OD/ID stainless steel needle placed perpendicular to $B_0$ in a gel phantom at 3 Tesla. More particularly, FIG. 9 illustrates 0.5 mm in-plane resolution, 3D FSE-based MSI images of a stainless steel needle in a gel phantom using 0, 250, 500, 750 and 1000 Hz offsets, 2 kHz $RF_{BW}$. The SSQ image shows significantly more information around the needle than the GRE image. In comparison, the SSQ image recovers information very close to the needle that is not visible with GRE. A field map was generated using the center of mass method from the MSI images. Each MSI image took 2 m, 27 s to generate. Each image is acquired in a separate acquisition. For faster imaging, the interleaved MSI sequence can be implemented where all frequency bins are imaged in each TR. The measured fields will be matched with the simulations of Aim 1a and significant deviations between simulations and measurements will guide refinements of the simulation model and the imaging method. 3D GRE with field mapping may be performed for comparison as it is an important sequence for iMRI applications.

2b. Shim Insert Fabrication: For safety and biocompatibility, the proposed shim coil design will be an insert that is fully insulated from the needle as well as the tissue. The shim inserts will be built by laying high gauge enameled copper wire along model-predicted shim coil paths upon thin wall miniature polyimide tube formers. Off-the-shelf 15 G (OD/ID 1.51/1.45 mm)-20 G (OD/ID 0.96/0.8 mm) polyimide tubes will be used as formers. One layer of insulating material such as Kapton® tape will be laid between individual coil overlap points and between the outermost coil and the needle's (or its shaft's) inner surface. A handheld 3D scanner (EXAscan Scanner) will be used to verify the accuracy of coil placement on the former. The leads will be marked and connected to a connector box at the base of the needle (FIG. 8c). The connector box will include inductively coupled or wireless probes for real-time orientation determination, monitoring, and current updates in the future.

Bench Tests: Prior to experiments in the scanner, the coils will be bench-tested with and without inserting the former in the needle. The coils will be connected to a constant current power supply and a Hall probe field sensor will be used to map the field around the insert. The measured field will be reconciled with simulated fields. Ideally, there should be no difference in the field with and without the metallic needle present. Fiber optic temperature probes will be used to measure coil heating and current constraints added if significant heating (>1° C. over 1 minute of continuous operation) is observed.

Figure 10:
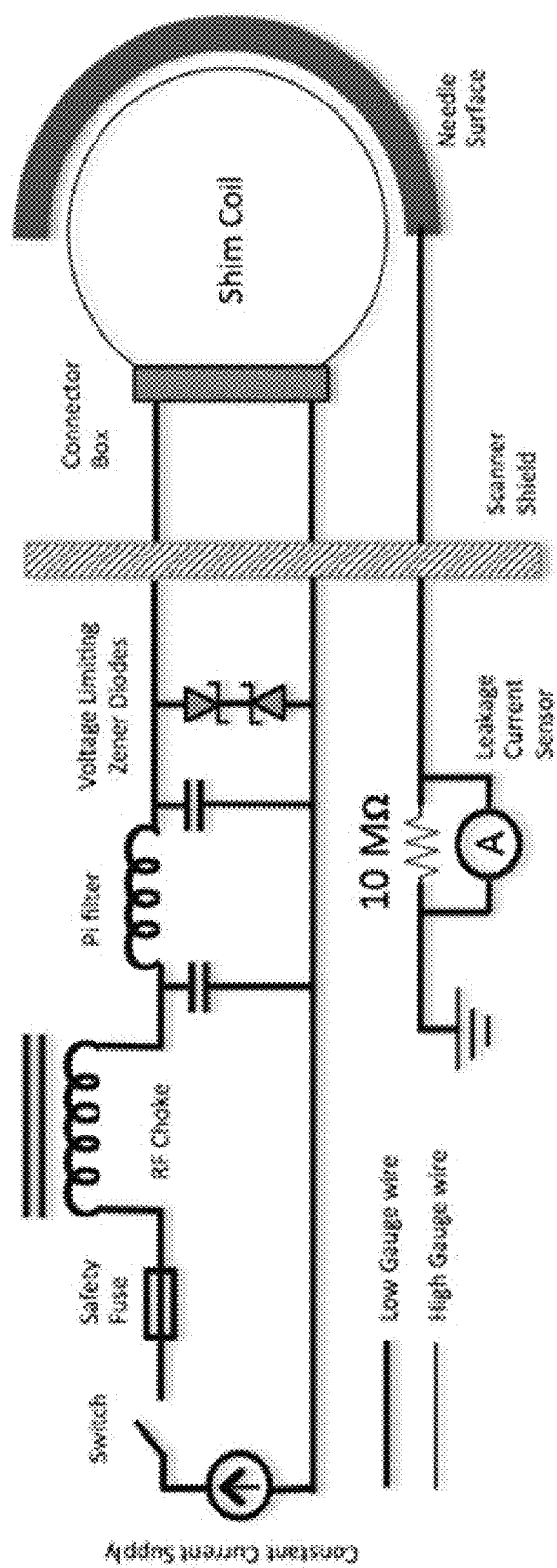
FIG. 10 is a schematic circuitry diagram illustrating a DC shim power supply system for each shim coil.

2c. Shim Current Supply: A single low-voltage (max ±5V/±1 A) differential constant-current shim power supply is used (FIG. 10). More particularly, FIG. 10 shows a schematic circuitry diagram illustrating a DC shim power supply system for each shim coil. An inline pi ripple filter and an RF choke may be added for filtering out gradient-induced ripples and RF-induced high frequency currents. Additional protection against bidirectional voltage spikes may be provided by back-to-back Zener diodes and a safety fuse. A switch may be added to turn on/off the system as required. The cabling from the instrumentation outside the scanner shield up to the connector box will be low gauge to minimize resistive losses. An optional leakage current circuit connecting to the needle's surface may be employed as a safety precaution for shim coil insulation leaks.

Shim Coil Calibration in Scanner: Oscilloscope measurements will be made to first make sure that the imaging gradient induced ripples are effectively suppressed by the filter and that high frequency AC is being blocked effectively. Following these tests, shim coil calibrations will be performed to estimate conversion constants in mTesla/Amp for the coils. For the calibration, the shim insert will be placed inside a polyethylene tube and placed in a gel phantom. The fields will be measured using the MSI sequence for the range of up to ±80% of wire carrying capacity in steps of ±10% and calibration constants derived from the data.

2d. Demonstration of Needle Shimming in a Gel Phantom: The final milestone in Aim 2 will be to demonstrate effective compensation of needle-induced $\Delta B_0$ and susceptibility artifacts. The needle with the shim insert will be placed inside a gel phantom in a full range of triaxial orientations using the workflow described in section 2a above and imaged with shims ON and OFF with MSI.

Evaluation of Shimming Efficacy and Success Metrics:

A combination of methods is used to evaluate the efficacy of artifact reduction, as follows: 1) the volume of the residual signal void in the SSQ images (defined as signal <10% of median signal) will be estimated for the shims ON and OFF cases and compared using a t-test. Shimming performance will be compared for different spans of frequency offsets (for example −250 to 250 Hz, −500 to 500 Hz and −1000 to 1000 Hz) using t-tests with successful shimming defined as significant (p<0.01) reduction of the signal void volume over all slices at a testing level of 0.05; 2) volume histograms of the 0 Hz offset FSE image will be compared. This method categorizes voxel signal intensities in different bands as signal void or pileup artifacts and compares histograms with and without metal artifact reduction; 3) field maps estimated from MSI may be compared with and without shims ON, within a range of expanding ROIs around the needle. Since the fields might have high kurtosis especially when comparing large ROIs, 80% and 50% inter-quartile ranges of the fields may be compared using t-tests. Successful shimming will be defined as significant (p<0.01) reduction of the field map 80% and 50% inter-quartile ranges at a testing level of 0.05; 4) a custom phantom may be 3D printed with insertion slots for the needles. Ultra-high molecular weight polyethylene needles will serve as gold standards. The voxel displacements of the phantom grid locations with and without shims ON will be compared; and 5) finally, 3D GRE images will be compared for signal voids using the t-tests, and field maps will be compared as described in item 3 above using the same significance levels.

Alternative Strategies: A limitation could be induced RF and gradient currents in the coils. Solutions to minimize these may provide local shim coils which can be integrated with head RF coils. Also, to ensure that there is no current leakage from the coils to the needle and tissue, an ammeter sensor in parallel with a high resistance can be added to the needle metal to monitor leakage currents. The mechanical torque on these coils is also expected to be minimal due to the small diameters, and low currents.

Aim 3: Demonstrate Compensation of Needle Artifact in Ex-Vivo Studies of Porcine Muscle.

In this aim, a compensation of artifacts in two different ex-vivo experiments is demonstrated: a biopsy-targeting study and an MR thermometry experiment. The goal in the first will be to show improved qualitative and quantitative visualization of tissue around the needle, and in the second will be to show improved precision of temperature measurements by image phase difference-based methods.

3a: Ex-vivo lesion targeting: 3D GRE imaging will be performed on a boneless pork loin sample. The images will be exported to a local computer and 10 target points will be selected randomly in the 3D image. The needle will then be inserted to required depths to reach the targets along the prescribed angles using the guide frame. MSI will be performed with the needle in place, with and without shims ON. In addition to the image evaluation using the protocol described in Section 2d above, qualitative comparison of the artifact will also be performed on a 5-point Likert scale where: 1=target point completely unreadable because of artifacts; 2=target point significantly affected; 3=apparent artifact near target point; 4=minor artifact at target point; and 5=no artifact. Differences in Likert score will be tested using the Wilcoxon signed-rank test. Images will be presented in a blinded and randomized manner for rating.

3b: Ex-vivo temperature precision measurement: Quantitative demonstration of artifact reduction will be performed with a proton resonance frequency (PRF) shift-based temperature measurement experiment. The PRF method uses phase changes in real-time to estimate temperature changes in tissue with reference to a baseline as:

$$\Delta T = \frac{\phi - \phi_{baseline}}{\gamma \alpha B_0 TE} \quad (2)$$

where $\phi$ and $\phi_{baseline}$ are the current and baseline image phases, $\alpha$ is $-0.01$ ppm/° C. is the PRF change coefficient for aqueous tissue. This experiment will not include heating, but focus on demonstrating improved precision of PRF shift temperature measurements from 3D phase maps. 3D GRE phase maps of ex-vivo tissue will be acquired on a setup similar to the one described above. The maps will be acquired continuously with a dynamic time series scan of 100 dynamics, with a defined baseline period of 25 images. Temperature changes will be estimated for every dynamic and an overall precision map of temperature will be calculated around the needle, with and without shims. Assuming the absence of heating, it is hypothesized that significantly higher precision of temperature measurements will be obtained with shims ON compared to the shims OFF. A one-sided t-test will be performed to demonstrate statistical significance.

Moving to Smaller Needle Sizes, Alternatives, and Conclusion.

For needle gauges higher than 9-14 G considered here, metal thin-film printing on flexible substrates may be considered. That will be key to minimizing space requirements and allowing a higher number of coils with more degrees of freedom. Printing of micrometer scale circuits on flexible substrates may be contemplated. That may be employed to print optimal shim coil paths to improve performance, minimize heating and adapt to smaller needle sizes. The artifacts scale with needle size and so will the necessary shim currents and wire gauges. Also, high conductivity oxygen-free copper wire may be considered.

In the embodiments above, the shim coils inserted inside the needle are powered through an external source. Alternatively, the power may be provided by a battery within, onboard, or operatively connected to the needle. In a further alternative, induction may be used to power the shim coils via an induction power source device positioned external to the body of the patient while the needle/shim coils are positioned within the body of the patient.

The coils may extend a portion of the longitudinal length of the needle or the entire longitudinal length of the needle. There may be at least one coil. In the case of two coils, they may be positioned 90° with respect to each other. Likewise, three coils would be positioned 60° from each other. A higher number of coils would be equally radially distributed as well.

The embodiments above describe the coil as being within the hollow shaft of the needle. However, the coil may be embedded within the circumferential wall of the needle (e.g., via a 3D printing process) or even positioned on an external surface of the needle. As described in the above embodiments, when placed within the hollow longitudinal shaft of the needle, the coils may be positioned on a former (that also extends along the longitudinal length of the needle) and are insulated from the internal space within the needle.

The field distortion induced by the probe scales linearly with the field strength of the MRI scanner. With a given coil configuration, an adjustment of current would produce a proportional amount of compensating field strength. A particular configuration of coils would be designed to take into account the size and shape of a particular needle.

The needle may be any gauge, for example 8-12 G, and may be used for imaging, monitoring, and procedures relating to, for example, biopsies (such as breast, prostate, head/brain, neck, musculoskeletal, spine, and liver biopsies), MR-guided ablation (which goes inside a patient's body and ablates a tumor using heat or cryo), MR probing, other therapies (such as brachytherapy), etc., for human patients or animals.

The active field compensation concept presented in this disclosure may also be applied to designing needles with reduced artifacts in simultaneous electrophysiology and functional MRI for animals. It is of high interest to perform electrode/needle-based electrophysiological measurements in animals at the same time as mapping brain activations using MRI. However, needle artifacts prevent robust fMRI recordings in these experiments. An actively shimmed needle/electrode design with reduced artifacts can therefore enable significantly more robust fMRI measurements in such animal experiments.

The application of a coil for purposes of compensation of magnetic field distortions can also be applicable to tools or implants other than needles. For example, instead of employing coils within a needle, the coils may be employed in implants (such as a hip implant) to correct field artifacts when placed within an MR field. The needle, tool, or implant may be employed in MR fields generated from other than iMRI devices as described in the embodiments above.

Embodiments are directed to an actively shimmed needle system for iMRI. The actively shimmed needle system comprises a needle comprising a shaft having a longitudinal axis. The actively shimmed needle system also comprises at least one shim coil that extends along the shaft in a direction substantially parallel to the longitudinal axis. The at least one shim coil is configured to have voltage applied thereto to compensate for magnetic field distortion generated by the needle when the actively shimmed needle system is positioned within an operating MRI device.

In an embodiment, the shaft is hollow. The at least one shim coil is positioned within an interior of the hollow shaft.

In an embodiment, the at least one shim coil comprises at least two shim coils equally radially distributed within the interior of the hollow shaft.

In an embodiment, the actively shimmed needle system may further comprise a power source positioned within the interior of the hollow shaft. The applied voltage is powered by the power source.

In an embodiment, the interior of the hollow shaft is defined by an inner surface of the hollow shaft. The actively shimmed needle system further comprises an insulating material positioned between an outermost coil of the at least one shim coil and the inner surface of the hollow shaft.

In an embodiment, the inner surface of the hollow shaft comprises a diameter, measured perpendicular to the longitudinal axis, in the range of 0.1 mm to 10 mm.

In an embodiment, the shaft is solid, and wherein the at least one shim coil is embedded within the solid shaft.

In an embodiment, the at least one shim coil is configured to have the voltage applied thereto in the range of −10 volts to +10 volts.

In an embodiment, the actively shimmed needle system is positioned within the MRI device operating in a range greater than or equal to 3 T.

In an embodiment, the shaft comprises a metal selected from the group consisting of stainless steel, titanium, Nitinol, brass, and combinations thereof.

Embodiments are also directed to a method of using an actively shimmed needle system for iMRI. The method comprises positioning an actively shimmed needle system within an operating MRI device. The actively shimmed needle system comprises a needle comprising a shaft having a longitudinal axis. The actively shimmed needle system also comprises at least one shim coil that extends along the shaft in a direction substantially parallel to the longitudinal axis. The method also comprises applying voltage to the at least one shim coil to compensate for magnetic field distortion generated by the needle when the actively shimmed needle system is positioned within an operating MRI device.

In an embodiment of the method, the shaft is hollow. The at least one shim coil is positioned within an interior of the hollow shaft.

In an embodiment of the method, the at least one shim coil comprises at least two shim coils equally radially distributed within the interior of the hollow shaft.

In an embodiment of the method, the method further comprises a power source positioned within the interior of the hollow shaft. The applied voltage is powered by the power source.

In an embodiment of the method, the interior of the hollow shaft is defined by an inner surface of the hollow shaft. The actively shimmed needle system further comprises an insulating material positioned between an outermost coil of the at least one shim coil and the inner surface of the hollow shaft.

In an embodiment of the method, wherein the inner surface of the hollow shaft comprises a diameter, measured perpendicular to the longitudinal axis, in the range of 0.1 mm to 10 mm.

In an embodiment of the method, the shaft is solid. The at least one shim coil is embedded within the solid shaft.

In an embodiment of the method, the voltage applied to the at least one shim coil is in the range of −10 volts to +10 volts.

In an embodiment of the method, the actively shimmed needle system is positioned within the MRI device operating in a range greater than or equal to 3 T.

In an embodiment of the method, the shaft comprises a metal selected from the group consisting of stainless steel, titanium, Nitinol, brass, and combinations thereof.

Although embodiments are described above with reference to an actively shimmed needle system positioned within the MRI device operating in a range greater than or equal to 3 T, the MRI device described in any of the above embodiments may alternatively operate in a range less than 3 T. Such alternatives are considered to be within the spirit and scope of the present invention, and may therefore utilize the advantages of the configurations and embodiments described above.

In conclusion, this disclosure solves an unsolved issue in MRI with a new approach. It utilizes specialized needle designs for use in multiple iMRI applications, as well as bolsters the advancement of iMRI in high and ultra-high field MRI.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. An actively shimmed needle system for interventional MRI (iMRI), the actively shimmed needle system comprising:
 a needle comprising a shaft having a longitudinal axis; and
 at least one shim coil that extends along the shaft in a direction substantially parallel to the longitudinal axis, wherein the at least one shim coil is configured to have voltage applied thereto to compensate for magnetic field distortion generated by the needle when the actively shimmed needle system is positioned within an operating MRI device.

2. The actively shimmed needle system of claim 1, wherein the shaft is hollow, and wherein the at least one shim coil is positioned within an interior of the hollow shaft.

3. The actively shimmed needle system of claim 2, wherein the at least one shim coil comprises at least two shim coils equally radially distributed within the interior of the hollow shaft.

4. The actively shimmed needle system of claim 2, further comprising a power source positioned within the interior of the hollow shaft, wherein the applied voltage is powered by the power source.

5. The actively shimmed needle system of claim 2, wherein the interior of the hollow shaft is defined by an inner surface of the hollow shaft, and wherein the actively shimmed needle system further comprises an insulating material positioned between an outermost coil of the at least one shim coil and the inner surface of the hollow shaft.

6. The actively shimmed needle system of claim 5, wherein the inner surface of the hollow shaft comprises a diameter, measured perpendicular to the longitudinal axis, in the range of 0.1 mm to 10 mm.

7. The actively shimmed needle system of claim 1, wherein the shaft is solid, and wherein the at least one shim coil is embedded within the solid shaft.

8. The actively shimmed needle system of claim 1, wherein the at least one shim coil is configured to have the voltage applied thereto in the range of −10 volts to +10 volts.

9. The actively shimmed needle system of claim 1, wherein the actively shimmed needle system is positioned within the MRI device operating in a range greater than or equal to 3 T.

10. The actively shimmed needle system of claim 1, wherein the shaft comprises a metal selected from the group consisting of stainless steel, titanium, Nitinol, brass, and combinations thereof.

11. A method of using an actively shimmed needle system for interventional MRI (iMRI), the method comprising:
 positioning an actively shimmed needle system within an operating MRI device, the actively shimmed needle system comprising:
  a needle comprising a shaft having a longitudinal axis; and
  at least one shim coil that extends along the shaft in a direction substantially parallel to the longitudinal axis; and
 applying voltage to the at least one shim coil to compensate for magnetic field distortion generated by the needle when the actively shimmed needle system is positioned within an operating MRI device.

12. The method of claim 11, wherein the shaft is hollow, and wherein the at least one shim coil is positioned within an interior of the hollow shaft.

13. The method of claim 12, wherein the at least one shim coil comprises at least two shim coils equally radially distributed within the interior of the hollow shaft.

14. The method of claim 12, further comprising a power source positioned within the interior of the hollow shaft, wherein the applied voltage is powered by the power source.

15. The method of claim 12, wherein the interior of the hollow shaft is defined by an inner surface of the hollow shaft, and wherein the actively shimmed needle system further comprises an insulating material positioned between an outermost coil of the at least one shim coil and the inner surface of the hollow shaft.

16. The method of claim 15, wherein the inner surface of the hollow shaft comprises a diameter, measured perpendicular to the longitudinal axis, in the range of 0.1 mm to 10 mm.

17. The method of claim 11, wherein the shaft is solid, and wherein the at least one shim coil is embedded within the solid shaft.

18. The method of claim 11, wherein the voltage applied to the at least one shim coil is in the range of −10 volts to +10 volts.

19. The method of claim 11, wherein the actively shimmed needle system is positioned within the MRI device operating in a range greater than or equal to 3 T.

20. The method of claim 11, wherein the shaft comprises a metal selected from the group consisting of stainless steel, titanium, Nitinol, brass, and combinations thereof.

* * * * *